(12) United States Patent
Sherrill et al.

(10) Patent No.: US 9,512,127 B2
(45) Date of Patent: Dec. 6, 2016

(54) PROCESS FOR THE PRODUCTION OF SPEHERICAL TETRANITROGLYCOURIL

(71) Applicant: U.S. Army Research Laboratory ATTN: RDRL-LOC-I, Adelphi, MD (US)

(72) Inventors: William Matthew Sherrill, Aberdeen, MD (US); Joseph Erik Banning, North East, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 142 days.

(21) Appl. No.: 14/499,280

(22) Filed: Sep. 29, 2014

(65) Prior Publication Data

US 2016/0090388 A1    Mar. 31, 2016

(51) Int. Cl.
*C07D 487/04*   (2006.01)
*C06B 25/34*    (2006.01)
*C06B 45/00*    (2006.01)

(52) U.S. Cl.
CPC ............. *C07D 487/04* (2013.01); *C06B 25/34* (2013.01); *C06B 45/00* (2013.01)

(58) Field of Classification Search
CPC ........ C07D 487/04; C06B 45/00; C06B 25/34
See application file for complete search history.

(56) References Cited

U.S. PATENT DOCUMENTS 4,487,938 A * 12/1984 Boileau ................ C07D 487/04
149/105

OTHER PUBLICATIONS

Sherrill et al. Propellants Explos. Pyrotech. 2014, 39, 670-676.*
Sherrill et al. Army Research Laboratory, ARL-TR-6940, May 2014, pp. i-12.*

* cited by examiner

*Primary Examiner* — Matthew Coughlin
(74) *Attorney, Agent, or Firm* — Robert Thompson

(57) ABSTRACT

A spherical morphology of the high explosive tetranitroglycoluril (TNGU) has been discovered. This new morphology exhibits approximately a twofold improvement in the response of the material to impact, more than a one and a half fold improvement in friction and the same high resistance to electrostatic discharge over non-spherical TNGU produced by other methods.

6 Claims, 2 Drawing Sheets

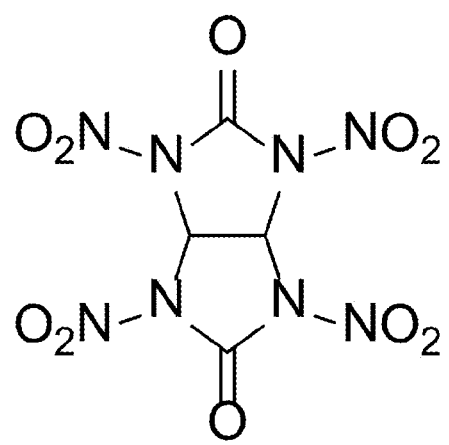
Figure 1. Tetranitroglycoluril (TNGU or Sorguyl)
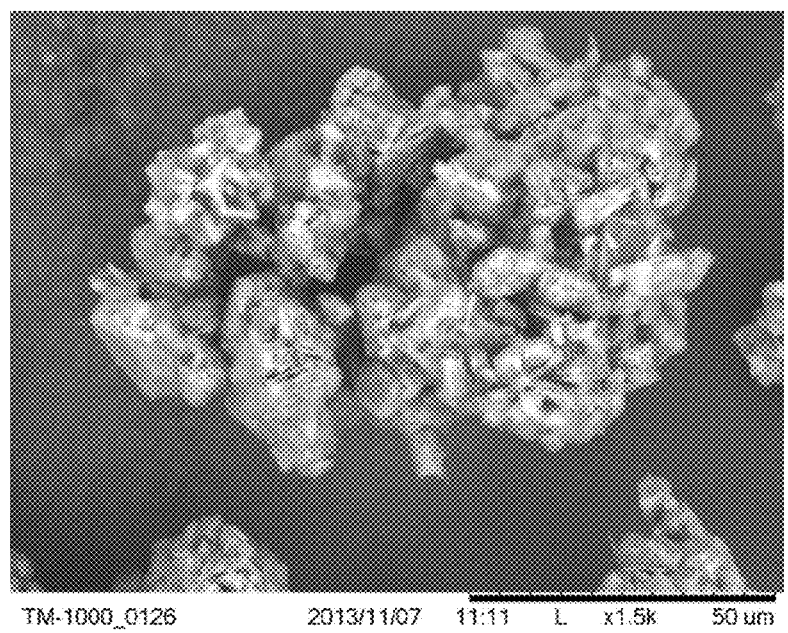
Figure 2. TNGU morphology as obtained from Ac$_2$O/HNO$_3$ literature procedure

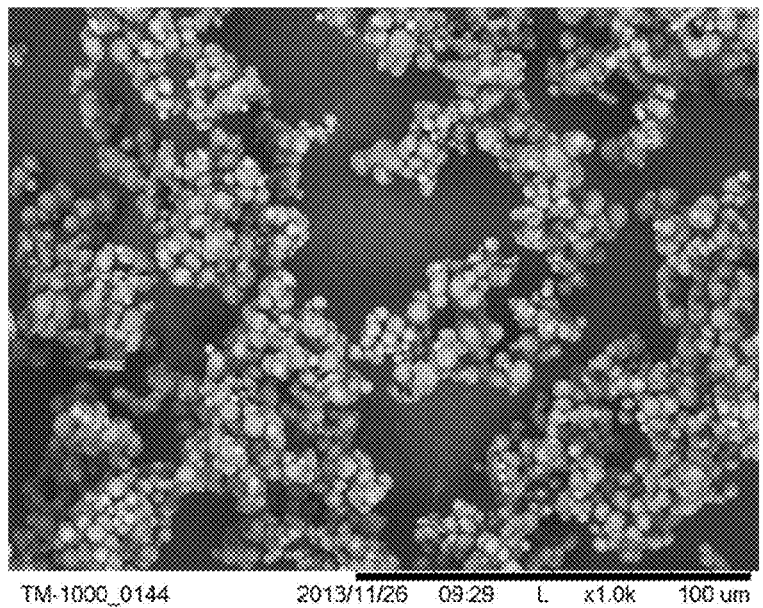
Figure 3
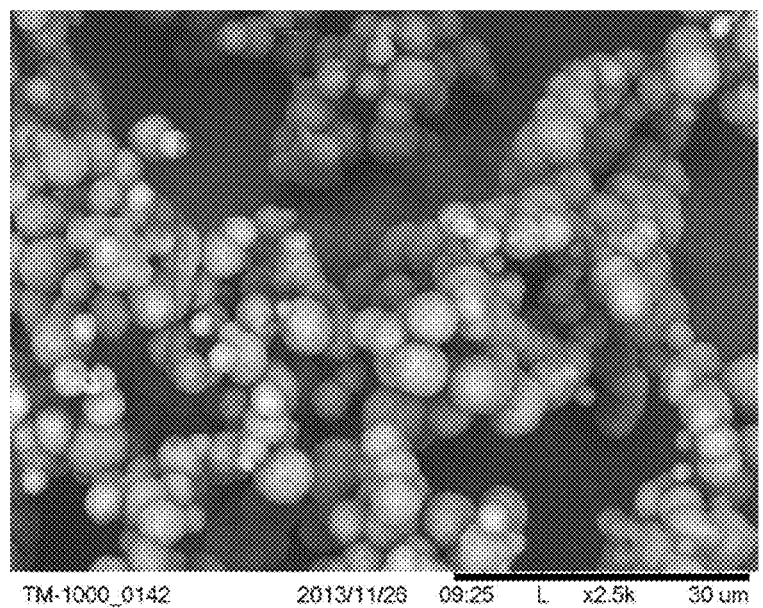
Figure 4. TNGU morphology as obtained after recrystallization from the $HNO_3$/DCM process.

PROCESS FOR THE PRODUCTION OF SPEHERICAL TETRANITROGLYCOURIL

GOVERNMENT INTEREST

The embodiments described herein may be manufactured, used, and/or licensed by or for the United States Government without the payment of royalties thereon.

BACKGROUND

Field of Use

The embodiments described herein generally relate to the chemistry and morphology of high energy materials and process methods thereof. Embodiments are also of use in applications requiring a high performing military grade explosive. Tetranitroglycoluril (TNGU) has a detonation performance exceeding Octahydro-1,3,5,7-tetranitro-1,3,5,7-tetrazocine (HMX) and could potentially be used in many of the same types of applications.

While structure 1 is a very powerful explosive, it has several disadvantages that have precluded its adoption as a standard military explosive. The first of these is its inherent instability in the presence of water. Due to the extreme electron deficiency of the carbonyl of the dinitrourea moiety, that center is incredibly susceptible to nucleophilic attack even by water through exposure to a moist atmosphere. The reactivity of this dinitrourea is unaffected through substitution at the bridgehead position. Unfortunately, this means the half-life of TNGU exposed to the atmosphere with a relative humidity approaching 85% can be on the order of days making it difficult to incorporate into formulations intended for standard military applications (8). While this feature may eliminate it from consideration for standard munition fills, it is potentially finding uses in self-remediating formulations specifically designed to have short environmental residence times after deployment and to lessen the hazards associated with unexploded ordinance (UXO).

Known polynitramines such as 1,3,5-trintro-1,3,5-hexahydrotriazine (RDX) and 1,3,5,7-tro-1,3,5,7-tetraazacyclooctane (HMX) are high-energy, high-density explosive compounds. They can be prepared by nitrolysis of hexamine with nitric acid and other similar procedures. RDX was first synthesized in 1906 by Brunswig (German Patent No. 299,028). It came into significant use during World II. RDX has a very good thermal stability. It under goes no decomposition below 100° C. It begins to decompose only at a temperature above 160-170° C. Under vacuum and after 40 hours, only 0.2 and 0.8 cm$^3$ of gases evolve from a one gram sample of RDX at respectively 102° C. and 150° C. It melts with decomposition at 204° C., but its explosion temperature measured by heating at the rate of 5° C. per minute is 260° C. The density of hexogen is very high. The crystal density (theoretical density) is 1.82 g/cm$^3$ at 20 degrees C. but its highest practical density is only 1.72 g/cm$^3$. Its rate of detonation is 8,800 m/s at the theoretical density and 8,520 m/s at the highest practical density. HMX was only discovered and recognized as a valuable explosive during World War II.

Octogen has a very good thermal stability. It undergoes no decomposition below 100° C. It begins to decompose at a temperature higher than that of Hexogen. Under vacuum and after 40 hours only 0.08, 0.09, and 0.12 cm$^3$ of gases evolve from a one gram sample at respectively 100, 120, and 150° C.

It melts with decomposition at 280° C. but its explosion temperature measured by heating at the rate of 5° C. per minute is 330° C.

The density of octogen is one of the highest reported for a crystalline high explosive. The crystal density is 1.91 g/cm$^3$ at 20° C. for the β-stable crystalline form but the highest practical density obtained by compression of powdered octogen is 1.84 g/cm$^3$. At this density, its rate of detonation is 8,850 m/s.

TNGU as obtained from prior art methods is obtained as small clumps of fine needles that appear to have significant gaps in between the needles (FIG. 2). This needle like morphology is similar to what was reported in the prior art. There are no other differences between the materials in the experimentally determined sensitivity, decomposition point, or chemical analysis.

In embodiments, one object of the present invention is to provide Tetranitroglycoluril having a spherical structure or morphology. This morphology is easily obtained through solvent/anti-solvent interactions by first dissolving the material in 100% nitric acid ($HNO_3$) and precipitating it by introducing it below the surface of dichloromethane (DCM). The size and quality of the spheres are determined by the rate of addition of the TNGU solution as well as the ratio of $HNO_3$ to DCM (table 1). It is worth noting, the only solvent system observed to generate spheres is an at least 98% $HNO_3$, DCM. In embodiments, a 100% $HNO_3$ solution is used. Using 90% $HNO_3$ or other solvents such as ethyl acetate, acetone, and acetonitrile with DCM as the anti-solvent does not result in the formation of spheres.

Research in the field of higher performing explosives for military use commenced and by the 2nd World War both pentaerythritol tetranitrate (PETN) and cyclotrimethylenetrinitramine (RDX) were investigated. RDX found greater use because it is less sensitive and more powerful than PETN.

The entirety of energetic materials is defined by the American Society for Testing and Material (ASTM) as " . . . a compound or mixture of substances which contains both the fuel and the oxidizer and reacts readily with the release of energy and gas . . . ". Energetic materials themselves are then divided into three unique classes: explosives, propellants and pyrotechnics. The class of explosives can be divided further into primary and secondary explosives.

Primary explosives are very sensitive explosives, which can be easily initiated by friction, impact, spark or heat. The initiation of primary explosives leads to a fast deflagration to detonation process with a shock wave formed, which is able to set off the less sensitive charge (main charge, secondary explosive) of an explosive device. They undergo a very fast deflagration to detonation transition (DDT) and are therefore used in initiating devices. Common primary explosives are lead(II) azide, lead(II) styphnate and mercury fulminate. The obvious disadvantage of these compounds is the toxicity of the heavy metal cations. Therefore, new less toxic primary explosives based on organic, metal free compounds were investigated and developed. Besides the development of metal free organic primaries, the replacement of the toxic cations with less toxic metals like silver, iron or copper is another topic of current interest.

Secondary explosives are not only much more stable in terms of friction, impact and electrostatic discharge, but also kinetically stable (metastable) compounds. Hence, they have to be ignited by much larger stimuli, mostly generated by a primary charge. After initiation by the detonation shockwave of primary explosives, the secondary explosive generates a shockwave which promotes the reaction front through the unreacted material. Although they need a much higher impetus to be detonated, secondary explosives exhibit much higher performances than primary explosives. Common secondary explosives are Trinitrotoluene (TNT), cyclotrimethylenetrinitramine (RDX), cyclotetramethylenetetranitramine (HMX), triaminotrinitrobenzene (TATB) and Nitroguanidine (NQ).

A spherical morphology of the high explosive tetranitroglycoluril (TNGU) has been discovered. This new morphology exhibits approximately a twofold improvement in the response of the material to impact, more than a one and a half fold improvement in friction sensitivity and the same high resistance to electrostatic discharge over non-spherical TNGU produced by other methods.

SUMMARY

According to this invention, the production of a spherical morphology of tetranitrogylcoluril (TNGU) is prepared starting with a non-spherical homogenous solution of TNGU in a solvent such as, for example, nitric acid ($HNO_3$) then precipitating the TNGU through the use of an anti-solvent to obtain TNGU with a spherical morphology.

BRIEF DESCRIPTION OF THE DRAWINGS

The embodiments herein will be better understood from the following detailed description with reference to the drawings, in which:

FIG. 1 illustrates a chemical structure for tetranitrogly-coluril (TNGU or Sorguly,1);

FIG. 2 illustrates the morphology of TNGU obtained by prior art methods;

FIG. 3 illustrates TNGU morphology obtained after recrystallization from the $HNO_3$/DCM procedure; and FIG. 4 illustrates another view of the TNGU morphology obtained after recrystallization from the $HNO_3$/DCM procedure.

DETAILED DESCRIPTION

The embodiments herein and the various features and advantageous details thereof are explained more fully with reference to the non-limiting embodiments that are illustrated in the accompanying drawings, examples and detailed in the following description.

In embodiments, this disclosure provides a new spherical structure or morphology produced in the synthesis of tetranitroglycoluril (TNGU). TNGU having the structure

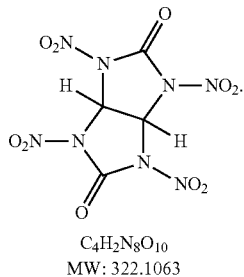

$C_4H_2N_8O_{10}$
MW: 322.1063

While many other morphologies of TNGU have been reported, this appears to be the first time a spherical morphology of the material has been described. This morphology is easily obtained through solvent/anti-solvent interactions by first dissolving the material in an at least 98% nitric acid ($HNO_3$) and precipitating it by introducing it below the surface of dichloromethane (DCM). The DCM may range from about 95 to about 100%. The size and quality of the spheres is determined by the rate of addition of the TNGU solution as well as the ratio of $HNO_3$ to DCM (Table 1). Using 90% $HNO_3$ or other solvents such as ethyl acetate, acetone, and acetonitrile with DCM as the anti-solvent has not been shown to result in the formation of spheres.

TABLE 1

Optimization of Sphericalization Procedure

| Scale (milligram [mg]) | $HNO_3$ (mL) | DCM (mL) | Stir Rate (RPM) | Morphology |
| --- | --- | --- | --- | --- |
| 25 | 0.025 | 1 | 0 | Cubes |
| 25 | 0.025 | 10 | 0 | Spheres and needles |
| 25 | 0.025 | 10 | 500 | Spheres |
| 640 | 6.4 | 100 | 500 | Spheres |
| 2270 | 22.7 | 200 | 500 | Spheres |

In aspects, the instant application discloses a novel spherical structure and synthesis of tetranitroglycoluril (TNGU) which produces spherical TNGU resulting in significantly decreased sensitivity of the explosive to external insult. The spherical morphology of TNGU is more than three times less sensitive to impact than TNGU produced via prior art methods. This new morphology of TNGU is also less sensitive to impact than HMX while having a higher energy content than HMX. The friction sensitivity of the spherical morphology is less sensitive than TNGU from the prior art, and is comparable to the friction sensitivity of HMX. The electrostatic discharge sensitivity is approximately four times less sensitive than HMX and similar to TNGU obtained via literature methods.

More specifically, by first making a homogenous solution of TNGU in a solvent such as, for example, 100% nitric acid ($HNO_3$) then precipitating the TNGU through use of an anti-solvent such as, for example, 100% dichloromethane (DCM) a spherical morphology of TNGU can be obtained. This spherical morphology has several properties which make it more desirable than other morphologies of TNGU that have been produced by the prior art. Previous methods of production of TNGU resulted in needle, or plate-like crystalline morphologies which are more sensitive compared to the spherical morphology. The spherical crystalline morphology greatly reduces hazards associated with the use of this high explosive. Synthesis of a new crystalline morphology of TNGU resulted in significantly decreasing the sensitivity of the explosive to external insult. This coupled with the improvement in the sensitivity profile of the material produced from the new process make it promising candidate as a feed stock in several high performance formulations in order to produce insensitive, high energy density formulations.

TNGU produced with the disclosed spherical structure is more than three times less sensitive to impact than TNGU produced by prior art methods. This difference in sensitivity profile makes the material isolated from the new process inherently more stable to handle and process than material isolated from the prior art methods.

This material is envisioned to be of use in applications requiring a high performing military grade explosive.

TNGU has detonation performance exceeding HMX and as such could potentially be used in many of the same types of applications.

Table 2 illustrates density, heat of formation, pressure, change in velocity, and oxygen bomb measurements for the spherical TNGU morphology, known TNGU morphology, RDX and HMX.

TABLE 2

Performance Predictions from Cheetah 6.0 Thermochemical Computer Code

| Substance | Density | $\Delta H_f$ (kJ/mol) | $P_{cj}$ (GPa) | $D_v$ (km/s) | $\Delta H_d$ (kJ/mL) | OB (%) |
|---|---|---|---|---|---|---|
| Spherical TNGU | 1.97[a] | 188.0[b] | 41.13 | 9.433 | 12.39 | +4.97 |
| TNGU[c] | 2.01 | 50.0 | 41.98 | 9.557 | 11.78 | +4.97 |
| RDX[c] | 1.816 | 70.01 | 33.42 | 8.858 | 10.41 | −21.61 |
| HMX[c] | 1.90 | 75.02 | 37.159 | 9.243 | 11.01 | −21.61 |

[a]Density measured by helium gas pycnometry
[b]Heat of formation measured by oxygen bomb calorimetry
[c]Heat of formation and density numbers obtained from Cheetah 6.0 database

TABLE 3

Sensitivity Data

| Substance | Impact (in.)[a] | Friction (N)[b] | ESD (J)[c] |
|---|---|---|---|
| Spherical TNGU | 13.04 | 70 | 3.25 |
| Non-Spherical TNGU | 4.05 | 63 | 3.25 |
| RDX | 9.08 | 120 | 0.625 |
| HMX | 9.08 | 120 | 0.025 |

[a]$H_{50}$ impact height determined on an apparatus using 2 kg weight by the Langlie one shot method
[b]Friction determined on a Julius Peter's BAM friction apparatus
[c]ESD determine using an ABL Laboratories ElectroStatic Discharge Apparatus The Impact Sensitivity of the Material Having a Spherical Morphology Produced Via the New Method Physical Properties:

Density of Spherical TNGU from helium gas pycnometry: 1.97 g/cc

Particle size distribution: ≥3 micron

Differential Scanning Calorimetry Peak decomposition: 220° C. at 10° C./min heating ramp Analytical data: Matches with samples prepared according to the prior art.

EXAMPLES

Example 1

General Procedure at the 2 Mmol Scale

TNGU (640 mg, 2 mmol) prepared via prior art literature methods, is dissolved in 6.4 mL of greater than or equal to 98% nitric acid ($HNO_3$) at from about 20 to about 25° C. This homogenous solution is then introduced below the surface to a stirring beaker of from about 90 to about 110 ml dichloromethane (DCM) at a rate of from about 0.5 to about 1.5 mL/min. Once the addition is completed, stirring is stopped, and the TNGU settles to the bottom of the beaker. The supernatant is decanted, the TNGU is resuspended in approximately 25 mL of DCM and then allowed to settle. This washing procedure with DCM is repeated from about four to about six times until none of the $HNO_3$ remains. The TNGU is then vacuum dried to remove the residual DCM and stored in a dessicator over Drierite®. The amount of spherical TNGU recovered from this process is 462 mg (1.43 mmol, 72%). Scanning electron microscopy of the material from this process stirring at a rate of 250 RPM yields spheres equal to or greater than 3 microns in diameter. In other embodiments, the spherical particle size may range from 3 to 10 microns in diameter. Various particle sizes can be obtained through various stirring rates. Analytical data match with that of samples prepared according to literature methods.

Example 2

A Typical Procedure at the 7 Mmol Scale

TNGU (2.27 grams, 7 mmol) prepared via the prior art literature methods is dissolved in 22.7 mL of greater than or equal to 98% nitric acid $HNO_3$ at from about 20 to about 25° C. This homogenous solution is then introduced below the surface to a stirring beaker of from about 190 to about 210 ml of dichloromethane (DCM) at a rate of from about 0.5 to about 1.5 mL/min. Once addition is completed, stirring is stopped, and the TNGU settles to the bottom of the beaker. The supernatant is decanted, the TNGU is resuspended in about 50 mL of DCM then allowed to settle. This washing procedure is repeated from about four to about six times until none of the $HNO_3$ remains. The TNGU is then vacuum dried to remove the residual DCM and stored in a dessicator over Drierite®. The amount of spherical TNGU recovered from this process is 1.66 g (5.15 mmol, 73%). Scanning electron microscopy of the material from this process stirring at a rate of 250 RPM yields spheres equal to or greater than 3 microns in diameter. In other embodiments, the particle size may range from about 3 to about 10 microns in diameter. Various particle sizes can be obtained through various stirring rates. Analytical data match with that of samples prepared according to literature methods.

NMR spectra were recorded on a Brüker 600 MHz NMR with acetone-d6 as the solvent. All NMR chemical shifts are reported in ppm relative to TMS-Cl. FTIR spectra were recorded using a Brüker Alpha-T fitted with a diamond ATR (DATR) cell. Density was measured using gas pycnometry on a Micromeritics AccuPyc 1330 using helium as the analysis gas. Differential scanning calorimetry (DSC) was performed on a TA instruments Q10 or Q20 calorimeter calibrated to the melting point of indium. $H_{50}$ values for drop weight testing were determined using the Langlie one-shot method on a tester dropping a 5 lb weight from a maximum height of 60 in. Friction sensitivity measurements were determined on a BAM friction tester and ESD was determined using an ABL ESD apparatus. All deuterated solvents were obtained from Cambridge Isotope Laboratories, Andover, Mass., USA. All other materials used were obtained from Sigma Aldrich Corp. St. Louis, Mo., USA and were used as received unless otherwise noted.

Some properties of structure 1 obtained via our method:
Density of Spherical TNGU from helium gas pycnometry: 1.97 g/cc Particle size distribution: ≥3 micron Differential Scanning calorimetry Peak decomposition: 220° C. at 10° C./min heating ramp The original patent for structure 1, FIG. 1 was granted in 1984 to J. Boileau. His synthetic methodology for successfully achieving 1 was the direct nitration of glycoluril using a mixture of $N_2O_5$ and 100% $HNO_3$. The yields on his process are claimed to be greater than 85%. It has since been discovered it is possible to successfully synthesize structure 1 using a mixture of acetic anhydride and 100% $HNO_3$ in similar yields without necessitating the making $N_2O_5$ directly. Both of these methods yield structure 1 that is highly sensitive to impact and friction (approximately twice more sensitive on both accounts than standard military explosives RDX and HMX) making handling of the material from these processes inherently more dangerous.

What is claimed is:

1. A process for preparing an at least seventy percent (70%) yield of a spherical tetranitroglycoluril (TNGU) by recrystallization comprising the steps of:
    a) dissolving an amount of tetranitroglycoluril (TNGU) in a 100% solution of nitric acid ($HNO_3$) at a temperature of from about 20 to about 25 degrees Celsius to produce a homogeneous solution;
    b) stirring the solution while adding below the solution surface, from about 90 to about 100 milliters of a dichloromethane solvent;
    c) decanting the supernatant and re-suspending the TNGU in from about 20 to 30 milliliters of the dichloromethane solvent and allowing the precipitated spherical TNGU to settle;
    d) washing the precipitated spherical TNGU with from about 20 to 30 milliliters of the dichloromethane solvent four to six times until none of the nitric acid remains; and
    e) vacuum drying the resultant spherical TNGU and storing in a dessicator.

2. The process according to claim 1 wherein the spherical tetranitroglycoluril (TNGU) has a diameter of greater than 3 microns.

3. The process according to claim 1 wherein the spherical tetranitroglycoluril (TNGU) has a diameter of from greater than 3 microns to about 10 microns.

4. The process of claim 1 wherein the dichloromethane is added at a rate of about 1 milliliter per minute until the addition of dichloromethane is complete.

5. The process of claim 1 wherein the dichloromethane solvent is 100% dichloromethane.

6. The process of claim 1 wherein the temperature of the tetranitroglycoluril (TNGU) and nitric acid solution is 25 degrees Celsius.

* * * * *